United States Patent [19]
Kaloyeros et al.

[11] Patent Number: 6,099,903
[45] Date of Patent: Aug. 8, 2000

[54] MOCVD PROCESSES USING PRECURSORS BASED ON ORGANOMETALLOID LIGANDS

[75] Inventors: Alain E. Kaloyeros, Slingerlands; John T. Welch, Albany; Paul J. Toscano, Schenectady; Rolf Claessen, Albany, all of N.Y.; Andrei Kornilov, Kiev, Ukraine; Kulbinder Kumar Banger, Albany, N.Y.

[73] Assignee: Research Foundation of State University of New York, Albany, N.Y.

[21] Appl. No.: 09/314,762

[22] Filed: May 19, 1999

[51] Int. Cl.$^7$ .............................. C23C 16/18; C23C 16/06
[52] U.S. Cl. .......................... 427/250; 427/123; 427/124; 427/125
[58] Field of Search ................................. 427/250, 248.1, 427/123, 124, 125

[56] References Cited

U.S. PATENT DOCUMENTS 5,698,022  12/1997  Glassman et al. .
5,820,664  10/1998  Gardiner et al. .................... 106/287.17
5,840,897  11/1998  Kirlin et al. ................................ 546/2

OTHER PUBLICATIONS

"Some Bifunctional Acylisilanes and Their Photochemical Reactions", Gasking et al; J. Chem. Soc. Perkin Trans., 1985, pp. 409–413.

"Synthesis of acylsilanes via transmetalation of 1–triorganosilyloxyvinyltin derivatives", Verlhac et al., Journal of Organometallic Chemistry, 437 (1992) pp. C13–C18.

"Synthesis and the electronics spectra of the first β–Ketoacylsilanes and their lithium enolates; new insights into hyperconjugation in acylsilanes and their enolates", Apeloig et al., Jpurnal of Organometallic Chemistry, 449 (1995) pp. 73–82.

"Synthesis of Functional Acylsilanes from Carboxylic Acid Chlorides and Sily Zinc Cyanocuprates"Bonini et al., Synthesis, Jan. 1995, pp. 92–96.

"Divergent Response of a Hindred Cyclopropene to Strong Oxdizing Agents", Maynard et al., J. Org. Chem. 1991, 56, pp. 5480–5482.

"Synthesis of New Functionalized bis–Acylsilanes. β–Hydroxy–and β–oxo–bis–acylsilanes", Bouillon et al., Tetrahedron Letters, vol. 38, No. 37, pp. 6595–6598, 1997.

"Synthesis and Reactions of Silyl and Germy Derivatives of Scandocene. Structure of $Cp_2Sc[Si (SiMe_3)^3](THF)$", Campion et al., Organometallics 1993, 12, pp. 2584–2590.

"Synthesis and Characterization of Alkaline–Earth–Metal β–Diketonate Complexes Used as Precurors for Chemical Vapor Deposition of Thin–Film Superconductors", Turnipseed et al., Inorg. Chem. 1991, 30, pp. 1164–1170.

"A Simple Method of Dethioacetalization", Stork et al., Tetrahedron Letters, vol. 30, No. 3, pp. 287–290, 1989.

"Reaction of Lithium Dialkly–and Diarylcuprates with Organic halides", Whitesides, et al., Journal of the America Chemical Society, 91:17, Aug. 13, 1969, pp. 4871–4882.

"Conjugate Addition of trimethylsilylithium. A Preparation of 3–Sily Ketones"Still, J. Org. Chem., vol. 41, No. 18, 1976, pp. 3063–3064.

*Primary Examiner*—Roy V. King
*Attorney, Agent, or Firm*—Heslin & Rothenberg, P.C.

[57] ABSTRACT

Chemical vapor deposition processes utilize as precursors volatile metal complexes with ligands containing metalloid elements silicon, germanium, tin or lead.

25 Claims, No Drawings

MOCVD PROCESSES USING PRECURSORS BASED ON ORGANOMETALLOID LIGANDS

FIELD OF INVENTION

This invention relates to chemical vapor deposition processes utilizing organometalloid compounds and metal complexes thereof.

BACKGROUND OF THE INVENTION

As the microelectronics industry moves into ultralarge scale integration (ULSI), enhancement in performance speeds of integrated circuits will be achieved by reducing the device feature size and thereby the overall die size. As a result, density constraints will require multilevel structures with vertical interconnects. It is expected that the use of metals with lower resistivity, such as gold, silver and especially copper, will be necessary because of the submicron geometries.

Fabrication of interconnect structures includes one or more metallization steps. Metallization is commonly accomplished by physical vapor deposition (PVD) processes, including evaporating and sputtering. Chemical vapor deposition (CVD) processes have an advantage over these so-called "line of sight" processes in the fabrication of submicron vertical interconnects because conformal layers of metals are more easily produced.

In CVD, a volatile precursor, usually a complex of a metal with an organic ligand, serves as a source of the metal. The precursor is delivered to the substrate in the vapor phase and decomposed on the surface to release the metal. The precursor must exhibit sufficient thermal stability to prevent premature degradation or contamination of the substrate and at the same time facilitate easy handling. Vapor pressure, the adsorption/desorption behaviour, the chemical reaction pathways, the decomposition temperature can directly affect the purity of the deposited metal film and the rate of thin-film formation.

CVD precursors very frequently are based on complexes of metals with β-diketonates such as 2,2,6,6-tetramethyl-3,5-heptanedione (thd) and acetylacetonate (acac) and fluorinated β-diketonates, such as 1,1,1,5,5,5-hexafluoro-2,4-pentanedione (hfa or hfac) and 2,2-diethyl-6,6,7,7,8,8,8-heptafluoro-3,5-octanedione (fod). Volatility of the non-fluorinated precursors is insufficient for many applications. The fluorinated analogs possess greater volatility, but also have a tendency to fragment, a consequence of fluorine migration/carbon-fluorine bond cleavage at elevated temperatures, leading to contamination of the substrate. Consequently, a need exists for precursors which retain volatility yet release the metal without degradation of the ligand and for ligands which are not labile or disposed toward fragmentation.

It is therefore an object of this invention to develop metal complexes for CVD precursors that are highly volatile and yet stable at the sublimation point and also retain desirable processing features. It is a further object to develop ligands for use in CVD precursors which can induce high volatility in a metal and can release the metal without degradation of the ligand. It is a further object to provide new synthetic routes for the synthesis of these ligands from commercially available starting materials in good yields.

SUMMARY OF THE INVENTION

It has been surprisingly discovered that certain organic compounds containing silicon, germanium, tin or lead, when complexed with a metal, can induce high volatility in the metal complex. The resulting complexes are stable at the sublimation point and retain desirable processing features. The compounds have the structure of formula I:

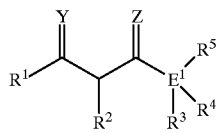

(I)

wherein $R^1$ is $C_2$ or higher alkyl, substituted alkyl, haloalkyl, cycloalkyl, $C_7$ or higher aryl, substituted aryl, heteroaryl, arylalkyl, alkoxy, acyl, alkyl carboxylate, aryl carboxylate, alkenyl, alkynyl, or $E^2(R^6)(R^7)(R^8)$;

$R^2$ is H, halogen, nitro, or haloalkyl;

$E^1$ and $E^2$ are independently Si, Ge, Sn, or Pb;

$R^3$, $R^4$, $R^5$, $R^6$, $R^7$, and $R^8$ are independently chosen from alkyl, substituted alkyl, cycloalkyl, aryl, substituted aryl, arylalkyl, alkoxy, alkenyl, alkynyl or $R^4$ and $R^5$, or $R^7$ and $R^8$ taken together form a divalent alkyl radical;

Y and Z are independently O, S or $NR^9$; and $R^9$ is alkyl, substituted alkyl, cycloalkyl, aryl, substituted aryl, heteroaryl, arylalkyl, alkoxy, alkenyl, or alkynyl.

The present invention also relates to metal-ligand complexes that are highly volatile and yet stable at the sublimation point. The complexes also retain desirable processing features. The metal complexes of the present invention have the structure of formula II:

wherein

M is a metal chosen from the group consisting of: Li, Na, K, Rb, Cs, Mg, Ca, Sr, Ba, Sc, Y, La, Ce, Ti, Zr, Hf, Pr, V, Nb, Ta, Nd, Cr, Mo, W, Mn, Re, Sm, Fe, Ru, Eu, Os, Co, Rh, Ir, Gd, Ni, Pd, Pt, Tb, Cu, Ag, Au, Dy, Ho, Al, Ga, In, Tl, Er, Ge, Sn, Pb, Tm, Sb, Bi, Yb, and Lu;

D is a neutral coordinating ligand;

n is equal to the valence of M;

p is zero or an integer from 1 to 6; and

L is a compound of formula III:

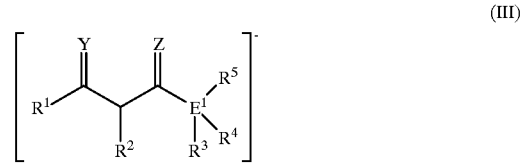

wherein $R^1$ is alkyl, substituted alkyl, haloalkyl, cycloalkyl, aryl, substituted aryl, heteroaryl, arylalkyl, alkoxy, acyl, alkyl carboxylate, aryl carboxylate, alkenyl, alkynyl, or $E^2(R^6)(R^7)(R^8)$;

$R^2$ is H, halogen, nitro, or haloalkyl;

$E^1$ and $E^2$ are independently Si, Ge, Sn, or Pb;

$R^3$, $R^4$, $R^5$, $R^6$, $R^7$, and $R^8$ are independently chosen from alkyl, substituted alkyl, cycloalkyl, aryl, substituted aryl, arylalkyl, alkoxy, alkenyl, alkynyl or $R^4$ and $R^5$, or $R^7$ and $R^8$ taken together formn a divalent alkyl radical; Y and Z are independently O, S or $NR^9$; and $R^9$ is alkyl, substituted alkyl, cycloalkyl, aryl, substituted aryl, heteroaryl, arylalkyl, alkoxy, alkenyl, or alkynyl.

In another aspect, the present invention relates to a method of depositing a metal-containing layer on a substrate comprising vaporizing a metal-ligand complex of formula II and decomposing the metal-ligand complex in the presence of the substrate.

DETAILED DESCRIPTION OF THE INVENTION

The present invention relates to organometalloid compounds that confer volatility on a metal when complexed therewith. Metalloids are defined herein as the elements silicon, germanium, tin and lead. Organometalloids are compounds containing one or more metalloid atoms bonded to a carbon atom. The organo-metalloid compounds of the present invention have the structure of formula I:

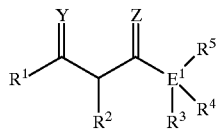

I wherein $R^1$ is $C_2$ or higher alkyl, substituted alkyl, haloalkyl, cycloalkyl, $C_7$ or higher aryl, substituted aryl, heteroaryl, arylalkyl, alkoxy, acyl, alkyl carboxylate, aryl carboxylate, alkenyl, alkynyl, or $E^2(R^6)(R^7)(R^8)$;

$R^2$ is H, halogen, nitro, or haloalkyl;

$E^1$ and $E^2$ are independently Si, Ge, Sn, or Pb;

$R^3$, $R^4$, $R^5$, $R^6$, $R^7$, and $R^8$ are independently chosen from alkyl, substituted alkyl, cycloalkyl, aryl, substituted aryl, arylalkyl, alkoxy, alkenyl, alkynyl or $R^4$ and $R^5$, or $R^7$ and $R^8$ taken together form a divalent alkyl radical;

Y and Z are independently O, S or $NR^9$; and $R^9$ is alkyl, substituted alkyl, cycloalkyl, aryl, substituted aryl, heteroaryl, arylalkyl, alkoxy, alkenyl, or alkynyl.

In a preferred embodiment, I is a silyl β-diketonate or a silyl β-thioketonate and $R^1$ is $C_2$ or higher alkyl, $C_7$ or higher aryl, or haloalkyl; $R^2$ is H; $R^3$, $R^4$, and $R^5$ are methyl; $E^1$ is Si; and Y and Z are independently O or S.

In a more preferred embodiment, $R^1$ is ethyl, isopropyl, n-propyl, isobutyl, n-butyl, t-butyl, trifluoromethyl, heptafluoropropyl, 2-propenyl or phenyl; $E^1$ is Si; and Y and Z are O or Y is S and Z is O.

In an even more preferred embodiment the compound is one of those appearing in Table 1:

TABLE 1

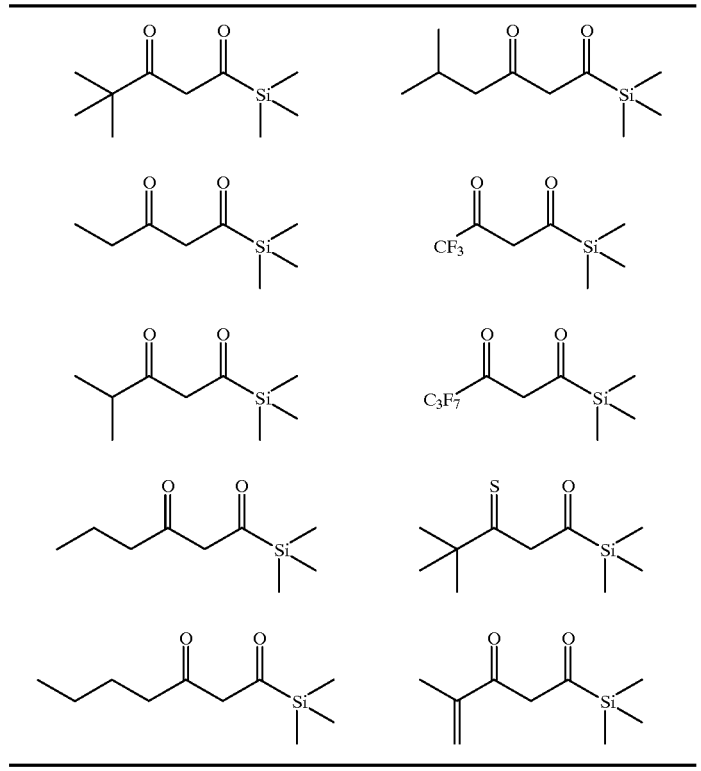

The volatile metal complexes of the present invention are useful in processes which deposit a metal on substrate from a vapor phase, such as metal organic chemical vapor deposition (MOCVD), molecular beam epitaxy (MBE) and atomic layer epitaxy (ALE). They have the structure of formula II:

$$ML_n \cdot pD \quad (II)$$

wherein

M is a metal chosen from the group consisting of: Li, Na, K, Rb, Cs, Mg, Ca, Sr, Ba, Sc, Y, La, Ce, Ti, Zr, Hf, Pr, V, Nb, Ta, Nd, Cr, Mo, W, Mn, Re, Sm, Fe, Ru, Eu, Os, Co, Rh, Ir, Gd, Ni, Pd, Pt, Tb, Cu, Ag, Au, Dy, Ho, Al, Ga, In, Tl, Er, Ge, Sn, Pb, Tm, Sb, Bi, Yb, and Lu;

D is a neutral coordinating ligand;

n is equal to the valence of M;

p is zero or an integer from 1 to 6; and

L is a ligand of formula III:

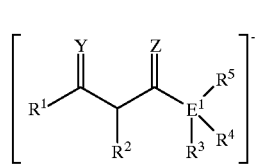

(III)

wherein $R^1$ is alkyl, substituted alkyl, haloalkyl, cycloalkyl, aryl, substituted aryl, heteroaryl, arylalkyl, alkoxy, acyl, alkyl carboxylate, aryl carboxylate, alkenyl, alkynyl, or $E^2(R^6)(R^7)(R^8)$;

$R^2$ is H, halogen, nitro, or haloalkyl;

$E^1$ and $E^2$ are independently Si, Ge, Sn, or Pb;

$R^3, R^4, R^5, R^6, R^7$, and $R^8$ are independently chosen from alkyl, substituted alkyl, cycloalkyl, aryl, substituted aryl, arylalkyl, alkoxy, alkenyl, alkynyl or $R^4$ and $R^5$, or $R^7$ and $R^8$ taken together form a divalent alkyl radical;

Y and Z are independently O, S or $NR^9$; and $R^9$ is alkyl, substituted alkyl, cycloalkyl, aryl, substituted aryl, heteroaryl, arylalkyl, alkoxy, alkenyl, or alkynyl.

Preferred metals are Cu, Co, Mn, Ag, In, Ce, Sr, Ba, Ru, or Au. More preferred metals are Cu and Ag. Preferred ligands are the preferred organometalloid compounds described above. Ligands having reduced oxygen content can reduce oxygen contamination of the substrate during metal deposition. Preferred metal complexes are listed in Table 2:

The metal complexes of the present invention may contain one or more neutral coordinating ligands (D in formula II) in addition to the organometalloid ligands described above, in particular when the metal has a valence of one. Suitable coordinating ligands include Lewis bases such as vinyltrimethylsilane (VTMS), bis(trimethylsilyl) acetylene, 1,5-cyclooctadiene (COD), 1,6-dimethyl-1,5-cyclooctadiene, alkyl phosphines, alkynes and mixtures thereof Synthetic methods for the preparation of β-diketones are numerous and well documented. However, application of these strategies to the synthesis of silyl β-diketonates is frequently unsuccessful, due to the reactivity of the product to the reagents or reaction conditions, and to the occurrence of side reactions via the cleavage of the carbonyl-silicon bond. Therefore, it is preferred that the organometalloid compounds of the present invention be prepared by the processes of the present invention.

The organometalloid compounds may be prepared by a Claisen condensation between a lithium enolate and an acyl, thioacyl or imino compound having a leaving group adjacent to the unsaturated group. This reaction is illustrated in Scheme 1:

SCHEME 1

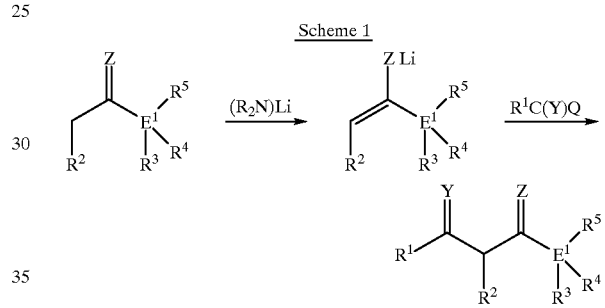

In Scheme 1, $R^1, R^2, R^3, R^4, R^5, R^6, R^7, R^8, R^9, E^1$, Y and Z are as defined for the compounds of formula I, above, R is alkyl, and Q is a leaving group. Suitable leaving groups for the process are halo, acyl, alkoxy, phenoxy, amido, dialkylamino and alkoxyamino. Preferably, $R^1C(Y)Q$ is an acid chloride or an ester.

In another embodiment, the organometalloid compounds are prepared as illustrated in Scheme 2. A thioketal-protected acylmetalloid is reacted with an alkyllithium compound, such as n-butyl lithium, and the product is subsequently reacted with a copper salt to form a protected lithium dithianylmetalloid cuprate. The cuprate is then reacted with an appropriate α-bromoketone or α-bromothioketone. The thioketal protecting group can be removed by methods described in the literature. Preferably the deprotection is accomplished by treatment with a suitable mercury reagent.

TABLE 2

| | |
|---|---|
| $Cu((CH_3)_3CCOCHCOSi(CH_3)_3)_2$ | $Cu(CF_3COCHCOSi(CH_3)_3)_2$ |
| $Cu((CH_3COCHCOSi(CH_3)_3)_2$ | $Cu((CH_3)_2CHCH_2COCHCOSi(CH_3)_3)_2$ |
| $Cu(CH_3CH_2COCHCOSi(CH_3)_3)_2$ | $Cu(CF_3(CF_2)_2COCHCOSi(CH_3)_3)_2$ |
| $Cu(CH_3CH_2CH_2COCHCOSi(CH_3)_3)_2$ | $Cu(C_6H_5COCHCOSi(CH_3)_3)_2$ |
| $Cu(CH_3(CH_2)_3COCHCOSi(CH_3)_3)_2$ | $Cu(H_2C=(CH_3)COCHCOSi(CH_3)_3)_2$ |
| $Cu((CH_3)_2CHCOCHCOSi(CH_3)_3)_2$ | $Co((CH_3)_3CCOCHCOSi(CH_3)_3)_3$ |
| $Ag((CH_3)_3CCOCHCOSi(CH_3)_3)$ | $Mn((CH_3)_3CCOCHCOSi(CH_3)_3)_3$ |

An example of an effective mercury reagent is a combination of mercuric oxide and mercuric chloride.

SCHEME 2

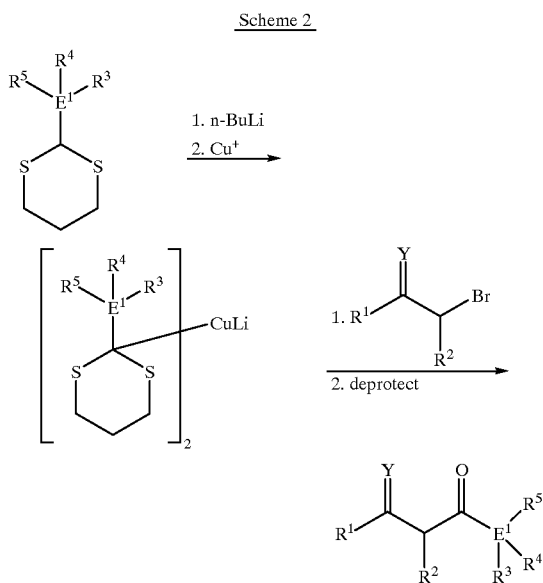

The metal complexes of the present invention may be prepared by reacting the organometalloid compounds synthesized as described above with a metal salt under protic or aprotic conditions. The ligand is dissolved in a suitable solvent and the anion of the ligand is formed by abstraction of a proton with base. The metal salt is then added, and the resulting metal ligand complex is isolated by removal of the solvent and crystallized. Under protic conditions, a protic base such as sodium hydroxide, may be used, with a protic solvent, such as an aqueous alcohol. Similarly under aprotic conditions, aprotic bases and solvents may be used. An example of a suitable aprotic solvent is tetrahydrofuran; an example of a suitable aprotic base is potassium hydride.

In another embodiment, the metal complexes may be prepared directly as shown in Scheme 3.

SCHEME 3

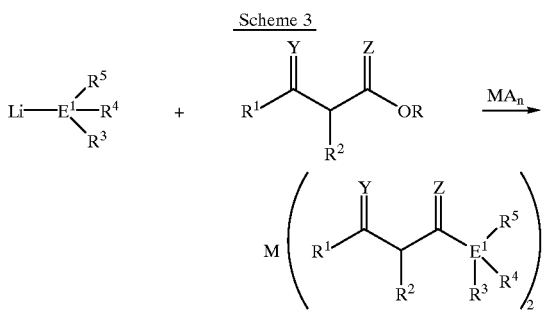

In Scheme 3, $R^1$, $R^2$, $R^3$, $R^4$, $R^5$, $R^6$, $R^7$, $R^8$, $R^9$, $E^1$, Y and Z are as defined for the compounds of formula I, above, and R is alkyl or phenyl. The starting lithium metalloid compound of formula $E^1R^3R^4R^5Li$ is prepared according to the method described in the literature, (Still, W. C., *J. Org. Chem.* 41, 3063–3064 (1976)). The lithiummetalloid compound is then reacted with an appropriate compound, for example, a β-diketone, a β-thioketone, or a β-keto-imine, to yield a ligand of formula I. Without isolating the product, a metal salt is added to form a complex of the metal with the ligand.

Processes whereby metals are deposited from volatile precursors are utilized in many different microelectronics applications. Metals such as Li, Na, K, Rb, Cs, Mg, Ca, Sr, Ba, Sc, Y, La, or Ce are typically used in applications such as high k dielectrics, superconductors, and high refractive index materials, although their use is not limited to these applications. Metals such as Ti, Zr, Hf, Pr, V, Nb, Ta, Nd, Cr, Mo, W, Mn, Re, or Sm are typically used in microelectronic applications chemically combined with nitrogen or silicon as the nitride or silicide for use as barrier materials or hard coatings, although, again, their use is not limited to these applications. Metals such as Fe, Ru, Eu, Os, Co, Rh, Ir, Gd, Ni, Pd, Pt, Tb, Cu, Ag, Au, Dy, Zn, Cd, Hg, Ho, Al, Ga, In, Tl, and Er are typically used in electronics applications as metals, or metal alloys, in particular, as metal or metal alloy films for interconnects, electrodes, and mirrors, although, again, their use is not limited to these applications. Metals and metalloids such as Si, Ge, Sn, Pb, Tm, Sb, Bi, Yb, and Lu are typically used in microelectronic devices and as semiconductors, although, again, their use is not limited to these applications.

The metal complexes of the present invention may be deposited on a substrate to form a layer of one or more metals in the form of the metal or of particular inorganic compounds, for example as an oxide, a hydroxide, a carbonate or a nitride. It will be apparent to a person skilled in the art that, if desired, he may use not only a particular compound of formula II but also mixtures of such compounds in which M, L, or both vary. A metal complex is advantageously decomposed in the vapor phase by a metal organic chemical vapor deposition (MOCVD), molecular beam epitaxy (MBE) or atomic layer epitaxy (ALE) process. The principle of these processes and suitable apparatuses for these purposes are well known in the art.

Typically, an apparatus for deposition from the vapor phase is pressure tight and can be evacuated. The substrate which is to be coated is to be introduced into this apparatus. Under reduced pressure the complex of formula II is vaporized. If desired, inert or reactive gas may be present in the apparatus in addition to the complex of the present invention in the vapor state.

The metal complex, in vapor form, is typically continuously or intermittently introduced into the apparatus via a special line. In some cases the metal complex may be introduced into the apparatus together with the substrate which is to be coated and not vaporized until it is within the apparatus. A carrier gas may optionally be used to aid in transporting the metal complex into the apparatus. The vaporization of the metal complex can be promoted by heating and if desired by the addition of the carrier gas.

Decomposition of the substrate may be effected by known methods. In general, these are thermal decomposition, plasma-or radiation-induced decomposition and/or photolytic decomposition.

Thermal decomposition from the vapor phase is usually performed so that the walls of the apparatus are kept cold and the substrate is heated to a temperature at which the desired layer is deposited on the substrate. The minimum temperature required for decomposition of the compound may be determined in each case by simple testing. Usually, the temperature to which the substrate is heated is above about 80° C.

The substrate may be heated in a conventional manner, for example, by resistance heating, inductive heating, or electric heating, or the substrates may be heated by radiation energy. Laser energy is particularly suitable for this. Laser heating is particularly advantageous in that lasers can be focused, and therefore can specifically heat limited areas on the substrate.

An apparatus for thermal chemical vapor deposition is typically pressure tight such as are used in high vacuum techniques as this process is typically carried out under reduced pressure. The apparatus may comprise gas lines which can be heated for carrying the metal complexes or the inner gas, blockable gas inlets and outlets, temperature measuring means if decomposition is to be induced by radiation, a radiation source must also be present.

In operation, the metal complex is introduced into the apparatus in the vapor phase. An inert or reactive carrier gas may be included.

Decomposition of the metal complex may be brought about as discussed above. For example, the decomposition may be plasma induced by a D.C. plasma, high-frequency plasma, microwave plasma or glow discharge plasma. Alternately photolytic decomposition may be effected by using a laser operating at a suitable wavelength.

The thickness of the layer deposited typically depends on the length of the deposition, on the partial pressure in the gas phase, on the flow rate of the gas and on the decomposition temperature. Depending on the desired layer thickness, a person skilled in the art can readily determine the time and deposition temperature required to produce a layer of a given thickness by simple tests.

If the metal complex is decomposed under an atmosphere of an inert gas, for example, argon, metal-containing layers are typically deposited in which the metal is in essentially metallic form. The decomposition may also be carried out under a reactive gas atmosphere, including a reducing atmosphere, an oxidizing atmosphere, and a hydrolyzing or carbonizing atmosphere. A reducing atmosphere with hydrogen as the reactive gas is typically used for deposition of layers containing metals, for example, copper metal. Where the decomposition is carried out under an oxidizing atmosphere, for example, one containing oxygen, nitrogen dioxide or ozone, layers containing the metal in the form of an oxide are formed. Alternatively, it is also possible to operate in a hydrolyzing or carbonizing atmosphere, for instance, in the presence of water and/or carbon dioxide. The metal carbonate or hydroxide which is produced as an intermediate stage may be subsequently calcined to form the metal oxide. In addition, use of ammonia as a reactive gas yields layers containing the metal in the form of a nitride.

The process according to the invention is also suitable for depositing layers which contain one or more metals. In this case, the deposition process is characterized in that for depositing layers containing more than one metal, one or more compounds of formula II or other formulas are decomposed simultaneously or successively.

EXAMPLES

Example 1

Preparation of $(CH_3)_3CCOCH_2COSi(CH_3)_3$ (IV) via Claisen Condensation of a Lithium Enolate and an Acid Chloride.

A two liter 3-neck flask held at 0° -C. was equipped with a magnetic stirrer, a rubber septum and a silicon oil bubbler under a positive flow of nitrogen gas. The flask was charged with anhydrous diethyl ether (250 mL) and diisopropylamine, (11.3 mL, 86.2 mmol), 2.5 M solution of n-BuLi in hexane (34.5 mL, 86.2 mmol) was added very slowly to the stirred solution. Once addition of the n-BuLi was complete the reaction temperature was maintained at 0° C. for 1 h to ensure generation of lithium diisopropylamide, (LDA). The temperature was lowered to −85° C. and acetyltrimethylsilane (10.0 g, 86.2 mmol), was then added slowly to the mixture. A smooth exothermic reaction ensued which resulted in the formation of corresponding organolithium anion, $(Me_3Si(C)(OLi)CH_2)$. A second one liter single-neck flask held at −110° C. equipped with a magnetic stirrer, a rubber septum and under a positive flow of nitrogen gas, was charged with anhydrous diethyl ether (250 mL) and trimethylacetylchloride, (10.6 mL, 86.2 mmol). After 10 minutes the labile trimethylsilylorganolithium anion, $(Me_3Si(C)(OLi)CH_2)$, was slowly transferred to the second flask via a cannula the reaction temperature was maintained between −110° C. and −75° C. After 1 hour, the reaction was essentially complete and was quenched with saturated ammonium chloride solution. Purification of the silyl β-diketonate was effected via flash column chromatography using a 100:1 (hexane: diethyl ether) eluant.

Example 2

Preparation of IV via Claisen Condensation of a Lithium Enolate and an Ester.

A two liter 3-neck flask held at 0° C. equipped with a magnetic stirrer, a rubber septum and a silicon oil bubbler and under a positive flow of nitrogen gas was charged with anhydrous diethyl ether (250 mL) and diisopropylamine, (11.3 mL, 86.2 mmol). n-Butyllithium (34.4 mL, 86.2 mmol, 2.5 M in hexane) was added very slowly to the stirred solution. Once addition of the n-BuLi was complete, the reaction temperature was maintained at 0° C. for 1 hour to ensure generation of lithium diisopropylamide, (LDA). The temperature was then lowered to −85° C. and acetyltrimethylsilane (10.0 g, 86.2 mmol) was added slowly to the mixture. A smooth exothermic reaction ensued which resulted in the formation of corresponding lithium enolate, $(Me_3Si(C)(OLi)CH_2)$. A second one -liter single-neck flask held at −110° C. equipped with a magnetic stirrer, a rubber septum and under a positive flow of nitrogen gas, was charged with anhydrous diethyl ether (250 mL) and methyl pivaloate, (10.6 mL, 86.2 mmol). After 10 minutes, the reactive lithium enolate, $(Me_3Si(C)(OLi)CH_2)$, was slowly transferred to this mixture via a cannula while the reaction temperature was maintained between −110° C. and −75° C. After 2 hours, the reaction was essentially complete and was then quenched with saturated ammonium chloride solution. Purification of the silyl β-diketonate was effected via flash column chromatography using a 100:1 (hexane:diethyl ether) solvent system.

Example 3

Preparation of IV via Pseudo Barbier Conditions.

Trimethylsilyllithium, (18 mmol) was prepared according to the literature method (Still, W. C., *J. Org. Chem.*, 41, 3063–3064 (1976)) and then transferred via cannula to a second reaction flask held at −78° C., charged with anhydrous diethyl ether, (150 mL) and methyl 4,4-dimethyl-3-oxopentanoate, $(CH_3)_3CCOCH_2CO_2CH_3$ (2.09g, 18 mmol), which resulted in the dissipation of the red colour. (Gasking, E. I.; Whitman, G. H. *J. Chem. Soc., Perkin Trans.* 1, 1985, 409–414) After 30 minutes the reaction was quenched with saturated ammonium chloride, (100 mL) and copper acetate (II) monohydrate, (3.60g, 18 mmol) was added to yield the crude silyl β-diketonate copper complex. Subsequent purification yielded pure metal complex.

Example 4
Preparation of IV by the Dithiane Route.

A 3-neck flask held at −30° C. was equipped with a magnetic stirrer, a rubber septum and a silicon oil bubbler was under a positive flow of nitrogen gas. The flask was charged with anhydrous THF (30 mL) and 2-trimethylsilane-1,3-dithiane, (3.8 mL, (20 mmol). n-Butyllithium (8.0 mL, 20 mmol, 2.5 M in hexane) was added very slowly to the stirred solution. Once addition of n-BuLi was complete the reaction temperature was maintained at −30° C. for 24 hour to ensure generation of 2-lithio-1,3 dithiane. The anion was transferred via a cannula to a second flask maintained at −60° C. and charged with an ethereal solution of $CuBr \cdot Me_2S$ (2.06 g, 10 mmol). After approximately one hour the formation of the 2-lithio-1,3-dithianylcuprate was essentially complete. Bromo pinacolone, $(CH_3)_3CCOCH_2Br$, dissolved in ether, was then added slowly to the organocuprate and was allowed to react for 24 hour at −30° C. The reaction was quenched with saturated ammonium chloride solution. Vacuum distillation (125–130° C., 0.5 mm Hg) afforded the pure product.

Deprotection of the dithiane protected silyl β-diketonate was achieved by treatment with mercuric oxide and mercuric chloride in an aqueous alcoholic solution for 1.5 hours, yielding the desired the silyl β-diketonate upon filtration and concentration.

Example 5
Formation of $Co((CH_3)_3CCOCHCOSi(CH_3)_3)_3$ under Protic Conditions.

A solution of IV (0.54 g, 2.7 mmol) prepared as in Example 1 in aqueous ethanol (80 mL) was prepared. To the stirred solution, an aqueous ethanolic solution of sodium hydroxide (0.1 g, 3 mmol) was slowly added and allowed to react approximately 15 minutes. The slow addition of this solution to cobalt (II) chloride hexahydrate, (0.30 g, 1.4 mmol) dissolved in aqueous ethanol resulted in the formation of a deep green solution. The solvent was removed in vacuo to leave behind the crude cobalt (III)silyl β-diketonate complex. Addition of pentane and water, followed by subsequent work-up and sublimation resulted in isolation of the analytically pure metal complex.

Example 6
Formation of $Cu((CH_3)_3CCOCHCOSi(CH_3)_3)_2$ under Aprotic Conditions.

Under aprotic conditions, IV (0.25 g, 1.3 mmol), prepared as in Example 1, was dissolved in THF (100 mL). To the stirred solution, potassium hydride, (KH), (0.05 g, 1 mmol) was added slowly and allowed to react for approximately 30 minutes. The addition of copper (II) chloride dihydrate, (0.11 g, 6.3 mmol) portionwise resulted in the formation of a deep green solution. The reaction was then quenched carefully with water and extracted with pentane. The solvent was then removed in vacuo to leave behind the copper (II) silyl β-diketonate complex, which on sublimation yielded the analytically pure metal complex.

Example 7
Formation of $Cu((CH_3)_3CCOCHCOSi(CH_3)_3)_2$ under Protic Conditions.

Under protic conditions, IV (0.25 g, 1.3 mmol), prepared as in Example 1, was dissolved in aqueous ethanol (80 mL). To the stirred solution, an aqueous ethanolic solution of sodium hydroxide (0.1 g, 3 mmol) was slowly added and allowed to react approximately 15 minutes. Copper (II) chloride dihydrate, (0.11 g, 6.3 mmol) was then added which resulted in the formation of a deep green solution. The solvent was then removed in vacuo to leave behind the copper (II) silyl β-diketonate complex. Sublimation resulted in the isolation of analytically pure metal complex.

Example 8
Direct Formation of $Cu((CH_3)_3CCOCHCOSi(CH_3)_3)_2$ using Crude IV To a stirred solution of crude IV (2.73g, 13.8 mmol) dissolved in THF (100 mL), a slurry of excess copper (II) acetate hydrate, (5.46 g, 27.4 mmol) in aqueous THF was added. Upon addition, a deep green solution formed. Extraction, washing, drying, and concentration resulted in isolation of a green oil. Column chromatography on silica gel using a 100:1 hexane-ether eluant system yielded semi-pure copper (II) silyl β-diketonate complex. Controlled sublimation resulted in the formation of analytically pure metal complex.

Example 9
Direct Formation of $Cu((CH_3)_3CCOCHCOSi(CH_3)_3)_2$ using Pure IV To a stirred solution of pure IV, (5.00 g, 25 mmol) dissolved in THF (100 mL), a slurry of copper (II) acetate hydrate, (3.00 g, 15 mmol) in aqueous THF was added. Upon addition, a deep green solution formed. Extraction, washing, drying, and concentration in vacuo resulted in isolation of the copper (II) silyl β-diketonate complex. Sublimation resulted in the formation of analytically pure metal complex.

Example 10
Preparation of $Cu(I)((CH_3)_3CCOCHCOSi(CH_3)_3) \cdot COD$

Under anaerobic conditions, 1,5-cyclooctadiene (0.1 g, 1 mmol) was added dropwise to a suspension of copper (I) chloride in THF. The suspension was stirred for 10 minutes, after which a solution of the potassium salt of IV (prepared by the addition of potassium hydride (0.05 g, 1 mmol) over 30 minutes to a solution of IV (0.25 g, 1.3 mmol)), was carefully added via syringe and allowed to react for approximately 3 hours. The resultant copper(I) silyl β-diketonate complex was isolated by subsequent anhydrous work-up.

Example 11
Formation of $Mn((CH_3)_3CCOCHCOSi(CH_3)_3)_3$ via Lewis Base.

A solution of IV (0.54 g, 2.7 mmol) in aqueous ethanol (80 mL) was prepared. To the stirred solution was slowly added an aqueous ethanolic solution of sodium hydroxide (0.1 g, 3 mmol). The resultant solution was stirred for approximately 15 minutes and then slowly added to manganese (II) chloride (0.176 g, 1.4 mmol) dissolved in aqueous ethanol which resulted in the formation of a dark green solution. The solvent was removed in vacuo to leave behind the crude manganese (III) silyl β-diketonate complex. Addition of pentane and water followed by subsequent work-up and sublimation yielded an analytically pure metal complex.

Example 12
Preparation of $Cu((CH_3)_3CCSCHCOSi(CH_3)_3)_2$ via Claisen Condensation of Lithium Enolate and Thioacid Chloride.

A two liter 3-neck flask held at 0° C. was equipped with a magnetic stirrer, a rubber septum and a silicon oil bubbler under a positive flow of nitrogen gas. The flask was charged with anhydrous diethyl ether (250 mL) and diisopropylamine (11.3 mL, 86.2 mmol). n-Butyllithium (34.5 mL of a 2.5 M solution in hexane, 86.2 mmol) was added very slowly to the stirred solution. Once the addition of BuLi was complete, the reaction temperature was held at 0° C. for 1 hour to ensure generation of lithium diisopropylamide, (LDA). The temperature was lowered to −85° C. and acetyltrimethylsilane (10.0 g, 86.2 mmol) was added slowly to the mixture. A smooth exothermic reaction ensued which resulted in the formation of corresponding organolithium enolate, (Me$_3$Si(C)(OLi)CH$_2$). A second one liter single-neck flask held at −110° C. and equipped with a magnetic stirrer, a rubber septum under a positive flow of nitrogen gas, was charged with anhydrous diethyl ether (250 mL) and trimethylthioacetylchloride, (10.6 mL, 86.2 mmol). After 10 minutes, the labile trimethylsilylorganolithium anion, (Me$_3$Si(C)(OLi)CH$_2$), was slowly transferred to the second flask via cannula while maintaining the reaction temperature between −110° C. and −75° C. After 1 hour the reaction was quenched with saturated ammonium chloride solution. Purification of the β-thioketoacyl-silane can be effected by flash column chromatography using a 100:1 (hexane:diethyl ether) eluant. The proton NMR spectrum of the product gave the expected results.

Example 13
Volatility of Metal Complexes with Silyl β-diketonates and Silyl β-thioketonates Thermogravimetric analysis (TGA) was performed on samples of the metal complexes listed in Table 3. The samples were heated at a rate of 10° C./min under an argon atmosphere. Weight loss was associated with transformation of the complexes into the vapor phase. The TGA curves showed rapid and complete volatilization of the complexes over a narrow temperature range, indicating the absence of decomposition under the conditions employed. The temperature at which 50% of the sample, by weight, has volatilized (T$_{50\%}$) is a measure of relative volatility, and is listed in the table for each compound. The T$_{50\%}$ values range from a low of about 111° C. for the fluorinated compound Cu(CF$_3$COCHCOSi(CH$_3$)$_3$)$_2$, to a high of about 170° C. for a complex with a phenyl-substituted ligand, Cu(C$_6$H$_5$COCHCOSi(CH$_3$)$_3$)$_2$.

TABLE 3

Volatility of Metal Diketonate Complexes

| Metal Complex | T$_{50\%}$, ° C. |
|---|---|
| Cu((CH$_3$)$_3$CCOCHCOSi(CH$_3$)$_3$)$_2$ | 158 |
| Co((CH$_3$)$_3$CCOCHCOSi(CH$_3$)$_3$)$_3$ | 167 |
| Mn((CH$_3$)$_3$CCOCHCOSi(CH$_3$)$_3$)$_3$ | 119 |
| Cu((CH$_3$COCHCOSi(CH$_3$)$_3$)$_2$ | 155 |
| Cu(CH$_3$CH$_2$COCHCOSi(CH$_3$)$_3$)$_2$ | 150 |
| Cu(CH$_3$CH$_2$CH$_2$COCHCOSi(CH$_3$)$_3$)$_2$ | 152 |
| Cu(CH$_3$(CH$_2$)$_3$COCHCOSi(CH$_3$)$_3$)$_2$ | 158 |
| Cu((CH$_3$)$_2$CHCOCHCOSi(CH$_3$)$_3$)$_2$ | 137 |
| Cu((CH$_3$)$_2$CHCH$_2$COCHCOSi(CH$_3$)$_3$)$_2$ | 161 |
| Cu(CF$_3$COCHCOSi(CH$_3$)$_3$)$_2$ | 111 |
| Cu(CF$_3$(CF$_2$)$_2$COCHCOSi(CH$_3$)$_3$)$_2$ | 120 |
| Cu(C$_6$H$_5$COCHCOSi(CH$_3$)$_3$)$_2$ | 170 |
| Cu(H$_2$C=(CH$_3$)COCHCOSi(CH$_3$)$_3$)$_2$ | 134, 234 |

Example 14
Chemical Vapor Deposition of Copper

Copper films were deposited on fragments of silicon wafers, including wafers having surfaces composed of silicon, silicon dioxide, patterned silicon dioxide, and tungsten nitride, using a copper (II) silyl β-diketonate precursor of composition Cu((CH$_3$)$_3$CCOCHCOSi(CH$_3$)$_3$)$_2$.

A cold wall stainless steel single wafer CVD reactor was employed for the depositions. The wafers were loaded into the chamber through a door and placed on a resistively heated stainless steel pedestal bearing a quartz plate and heated to 300° C. under a flowing hydrogen ambient atmosphere. The actual temperature of the wafer was measured via a thermocouple contacting the top side of the wafer. The system pressure was then reduced to the desired deposition pressure of 500 mTorr. The pressure was maintained throughout the time of the deposition using an automated throttle valve.

A source of the precursor was maintained at 140° C. The precursor was delivered to the reactor by means of a hydrogen carrier/reactant gas bubbler at a flow rate of 60 sccm at approximately 500 mTorr. After the deposition, the carrier gas flow was terminated, the source was closed to the reactor, and the chamber was evacuated to less than 20 mTorr and then flushed with nitrogen gas. The heater was allowed to cool under a flow of nitrogen. The test wafers were retrieved from the reactor through the door of the reactor.

The resulting copper films were smooth and exhibited high conformality at thicknesses ranging from 100 Å to 3000 Å (10 nm to 300 nm).

What is claimed:
1. A method of depositing a metal-containing layer on a substrate comprising:
(a) vaporizing a metal-ligand complex of formula II

$$ML_n\cdot pD \qquad (II)$$

wherein

M is a metal selected from the group consisting of: Li, Na, K, Rb, Cs, Mg, Ca, Sr, Ba, Sc, Y, La, Ce, Ti, Zr, Hf, Pr, V, Nb, Ta, Nd, Cr, Mo, W, Mn, Re, Sm, Fe, Ru, Eu, Os, Co, Rh, Ir, Gd, Ni, Pd, Pt, Tb, Cu, Ag, Au, Dy, Ho, Al, Ga, In, Tl, Er, Ge, Sn, Pb, Tm, Sb, Bi, Yb, and Lu;

D is a neutral coordinating ligand;

n is equal to the valence of M;

p is zero or an integer from 1 to 6; and

L is a ligand of formula III:

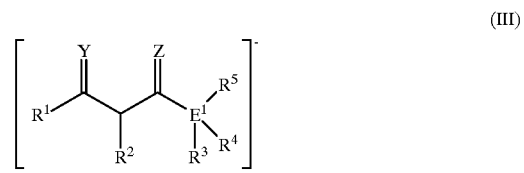

(III)

wherein

R$^1$ is alkyl, substituted alkyl, haloalkyl, cycloalkyl, aryl, substituted aryl, heteroaryl, arylalkyl, alkoxy, acyl, alkyl carboxylate, aryl carboxylate, alkenyl, alkynyl, or E$^2$(R$^6$)(R$^7$)(R$^8$);

R$^2$ is H, halogen, nitro, or haloalkyl;

E$^1$ and E$^2$ are independently Si, Ge, Sn, or Pb;

R$^3$, R$^4$, R$^5$, R$^6$, R$^7$, and R$^8$ are independently selected from alkyl, substituted alkyl, cycloalkyl, aryl, substituted aryl, arylalkyl, alkoxy, alkenyl, alkynyl or R$^4$ and R$^5$, or R$^7$ and R$^8$ taken together form a divalent alkyl radical;

Y and Z are independently O, S or NR$^9$; and

R$^9$ is alkyl, substituted alkyl, cycloalkyl, aryl, substituted aryl, heteroaryl, arylalkyl, alkoxy, alkenyl, or alkynyl; and (b) decomposing the metal-ligand complex in the presence of the substrate.

2. A method according to claim 1, wherein

R$^1$ is alkyl, aryl or haloalkyl;

R$^2$ is H;

$R^4$ is methyl;
$E^1$ is Si; and
Y and Z are independently O or S.

3. A method according to claim 2, wherein
$R^1$ is ethyl, isopropyl, n-propyl, isobutyl, n-butyl, t-butyl, trifluoromethyl, heptafluoropropyl, 2-propenyl or phenyl;
$R^2$ is H;
$R^4$ is methyl;
$E^1$ is Si; and
Y and Z are O or Y is S and Z is O.

4. A method according to claim 1, wherein M is Li, Na, K, Rb, Cs, Mg, Ca, Sr, Ba, Sc, Y, La, or Ce.

5. A method according to claim 1, wherein M is Ti, Zr, Hf, Pr, V, Nb, Ta, Nd, Cr, Mo, W, Mn, Re, or Sm.

6. A method according to claim 1, wherein M is Fe, Ru, Eu, Os, Co, Rh, Ir, Gd, Ni, Pd, Pt, Tb, Cu, Ag, Au, Dy, Zn, Cd, Hg, Ho, Al, Ga, In, Tl, or Er.

7. A method according to claim 1, wherein M is Si, Ge, Sn, Pb, Tm, Sb, Bi, Yb, Lu, Th or U.

8. A method according to claim 6, wherein M is Cu.

9. A method according to claim 8, wherein the metal-ligand complex comprises $Cu((CH_3)_3CCOCHCOSi(CH_3)_3)_2$.

10. A method according to claim 8, wherein the metal-ligand complex comprises $Cu((CH_3COCHCOSi(CH_3)_3)_2$.

11. A method according to claim 8, wherein the metal-ligand complex comprises $Cu(CH_3CH_2COCHCOSi(CH_3)_3)_2$.

12. A method according to claim 8, wherein the metal-ligand complex comprises $Cu(CH_3CH_2CH_2COCHCOSi(CH_3)_3)_2$.

13. A method according to claim 8, wherein the metal-ligand complex comprises $Cu(CH_3(CH_2)_3COCHCOSi(CH_3)_3)_2$.

14. A method according to claim 8, wherein the metal-ligand complex comprises $Cu((CH_3)_2CHCOCHCOSi(CH_3)_3)_2$.

15. A method according to claim 8, wherein the metal-ligand complex comprises $Cu((CH_3)_2CHCH_2COCHCOSi(CH_3)_3)_2$.

16. A method according to claim 8, wherein the metal-ligand complex comprises $Cu(CF_3COCHCOSi(CH_3)_3)_2$.

17. A method according to claim 8, wherein the metal-ligand complex comprises $Cu(CF_3(CF_2)_2COCHCOSi(CH_3)_3)_2$.

18. A method according to claim 8, wherein the metal-ligand complex comprises $Cu(C_6H_5COCHCOSi(CH_3)_3)_2$.

19. A method according to claim 8, wherein the metal-ligand complex comprises $Cu(H_2C=C(CH_3)COCHCOSi(CH_3)_3)_2$.

20. A method according to claim 6, wherein M is Co.

21. A method according to claim 20, wherein the metal-ligand complex comprises $Co((CH_3)_3CCOCHCOSi(CH_3)_3)_3$.

22. A method according to claim 5, wherein M is Mn.

23. A method according to claim 20, wherein the metal-ligand complex comprises $Mn((CH_3)_3CCOCHCOSi(CH_3)_3)_3$.

24. A method according to claim 6, wherein M is Ag.

25. A method according to claim 24, wherein the metal-ligand complex comprises $Ag((CH_3)_3CCOCHCOSi(CH_3)_3)$.

* * * * *